United States Patent [19]

Keegan et al.

[11] Patent Number: 5,718,695
[45] Date of Patent: Feb. 17, 1998

[54] WOUND PROTECTION DEVICE

[76] Inventors: Leo M. Keegan, 85 Norman Pl., Tenafly, N.J. 07670; Girard J. McSpiritt; Shari D. Rubinstein, both of 2 Maplehead Ct., Princeton Junction, N.J. 08550

[21] Appl. No.: 564,490

[22] Filed: Nov. 29, 1995

[51] Int. Cl.⁶ .......................... A61M 35/00; A61M 13/00
[52] U.S. Cl. .................. 604/290; 604/307; 602/46; 128/888
[58] Field of Search ...................... 128/888, 889; 604/289–290, 304–308; 602/41–59; 2/15; 606/216

[56] References Cited

U.S. PATENT DOCUMENTS

| 706,250 | 8/1902 | Muller | 128/888 |
| 3,026,874 | 3/1962 | Stevens | 128/888 |
| 4,212,296 | 7/1980 | Schaar | 128/888 |
| 4,709,695 | 12/1987 | Kohn et al. | 128/132 |
| 5,086,763 | 2/1992 | Hathman | 128/888 |
| 5,336,219 | 8/1994 | Krantz | 606/216 |

FOREIGN PATENT DOCUMENTS 4175  2/1893  United Kingdom .

*Primary Examiner*—John G. Weiss
*Assistant Examiner*—David J. Cho
*Attorney, Agent, or Firm*—Jacob M. Levine

[57] ABSTRACT

A wound protection device for protecting a wound the device being constructed to have a continuous outer wall, formed of a resilient material, surrounding a hollow, inner core. A first end of the device contacts intact skin surrounding the wound, the resiliency of the material protecting the surrounded would from forces associated with incidental contacts to the wounded area.

7 Claims, 1 Drawing Sheet

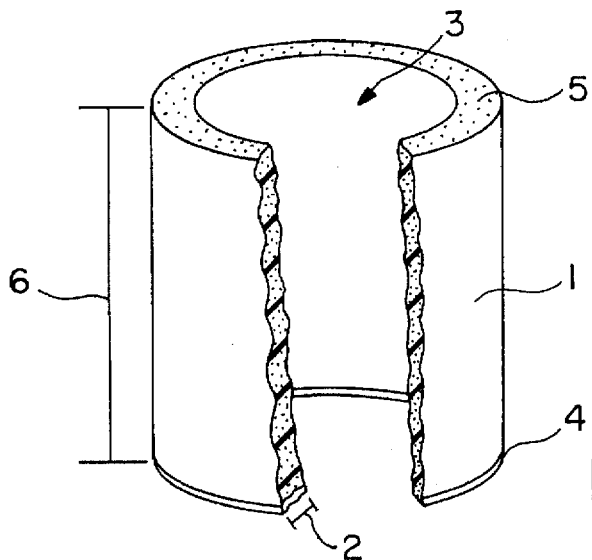
FIG. 1
FIG. 2A
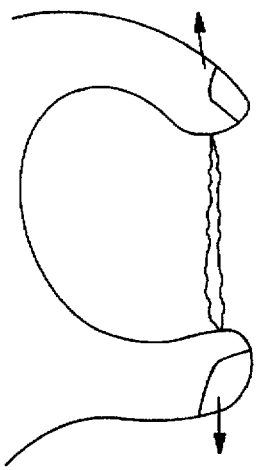
FIG. 2B
FIG. 2C-1    FIG. 2C-2
FIG. 2D
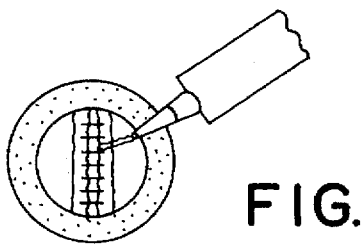
FIG. 2E

WOUND PROTECTION DEVICE

The present invention is directed to a wound protection device, and more specifically, to a device which allows for the quick healing of laceration—type wounds, with less scarring, by protecting the wound from a contact with forces associated with incidental contacts with the wounded area. The present invention is also directed to a method of treating such wounds, using the above-described device.

BACKGROUND OF THE INVENTION

The incidence of soft tissue injuries, particularly lacerations, is increasing. This phenomenon is particularly noticeable with regard to children. These injuries can result in severe scarring and disfigurement if not treated in an appropriate manner. In order to achieve an optimal aesthetic result, with the least amount of scarring, several factors must be addressed, including (1) perfect approximation of the wound skin edges (using suture or skin tape when necessary); (2) protection of the wound during healing until it achieves sufficient tensile strength to prevent wound dehiscence; and (3) avoidance of wound tension, which can result in a widening and enlarging of the resultant scar. Unfortunately, after a doctor's treatment, the wound maybe subjected to forces of numerous incidental contacts, such as those associated with falls and bumps with furniture and other people, particularly in the case of children. In addition, children have a strong tendency to touch the wound which further retards the healing process.

BRIEF DESCRIPTION OF THE INVENTION

In view of the forgoing, it is an object of the present invention to provide a device for protecting wounds, and particularly laceration-type wounds from forces associated with incidental contacts, after treatment, in order to improve the healing process. It is a further object of the invention to provide a wound protection device which allows a caregiver access to the wound, without removal of the device for visual inspection while also providing a means for the application of suitable ointments.

It is a still further object of the invention to describe a method of treating wounds, and particularly, laceration-type wounds in a manner which provides a speedy healing process, with minimal resultant scarring.

Other objects and features of the present invention will become apparent from the following detailed description, considered in conjunction with the accompanying drawings.

BRIEF DESCRIPTION OF THE DRAWINGS

FIG. 1 is a cut-away perspective view of the inventive wound protection device.

FIGS. 2a–2e illustrate the inventive method of treating a laceration-type wound.

DETAILED DESCRIPTION OF THE INVENTION

Referring to FIG. 1, there is shown the inventive wound protection device for protecting a wound to an animal and, particularly, laceration-type wounds to humans. The inventive device comprises continuous outer wall 1, formed of a resilient material having thickness 2 surrounding inner core 3. Preferably this material will be a moderately dense foam rubber. Wall 1 has first end 4 adapted to be placed in contact with intact skin of the animal surrounding the wound, and second end 5 distal from the animal. A distance between first end 4 and second end 5 defines length 6 of the device. This length 6, as wall as thickness 2 and the resiliency of the material from which the device is formed, is selected whereby, in combination, a force of an incidental contact with second end 5 will be dissipated by the material and a transmitted force, transmitted from first end 4 to the animal will be substantially reduced.

By incidental contacts, applicants refer to contacts with external forces a wound may normally encounter during the healing process, particularly with reference to children who are notorious for bumping the wound into furniture, or other children. An added advantage to the use of the device is that it aids in detering children from constantly touching the wound, an act well known to parents, pediatricians, and plastic surgeons.

Preferably, second end 5 will remain open to the exterior of the device to allow access to the wound. This not only allows for cleaning and the application of various topical ointments, such as antibiotics to the wound, but also provides the ability to visually inspect the wound during healing, without disturbing the dressing. By reducing the number of dressing changes, the physical discomfort and psychological trauma to the patient, again, particularly when the patient is a child, can be reduced. As tape, used to secure the device may impede this function, first end 4 will preferably be provided with adhesive layer 7 so that the device can be applied directly to the skin. With adhesive layer 7, the device can also be used to reduce tension on the healing wound, thereby preventing scar widening.

Referring now to FIGS. 2(a) through 2(e), the method of using the inventive device is illustrated. FIG. 2(a) shows a laceration-type wound. To treat the wound in the most preferable manner of the invention, and to reduce the resulting scar size, the edges of the wound are approximated, and tension on the wound is decreased by stretching the wound along it's axis, as shown in FIG. 2(b). While the inventive dressing can be applied at this time, so that the adhesive of the device maintains the tension on the wound, auxiliary securing steps such as suturing as shown in FIG. 2(c)-1, or taping with surgical (skin) tape (FIG. 2(c)-2) can be employed. Thereafter, the inventive device can be applied to the peripheral, intact skin, the raised profile of the device protecting the repaired wound from forces associated with incidental contacts, as described above. Topical ointments can then be applied and visual inspections of the wound can be made with the device in place, as shown in FIG. 2(d).

While only the fundamental novel features of the invention as applied to a preferred embodiment thereof have been shown and described, it is understood that various omissions, substitutions and changes in the form and details of the device and method illustrated, and in the operation thereof, may be made by those skilled in the art without departing from the spirit of the invention. It is therefore the intention of Applicants that the invention be limited only as indicated by the scope of the claims appended hereto.

We claim:

1. A method of protecting a laceration wound to an animal, said method comprising:

applying a wound protection device to skin of said animal, around a periphery of said wound, and securing said wound protection device to said animal, said wound protection device comprising a continuous outer wall formed of a resilient material having a thickness, surrounding an inner core, said wall having a first end adapted to be placed in contact with intact skin of said animal surrounding said wound, and a second end distal from said first end, a distance between said first end and said second end defining a length, said length, said thickness, and the resilience of said material being selected whereby, in combination, a force of an incidental contact with said second end will be dissipated by said material and a transmitted force, transmitted from said first end to said animal will be substantially reduced, wherein the skin surrounding said laceration is stretched to at least partially close said laceration before said device is applied.

2. The method of claim 1 wherein said device has an adhesive on said first end, said device being securable to said animal by pressing said first end to said skin.

3. The method of claim 1 wherein said animal is a human.

4. The method of claim 1 wherein edges of said laceration are approximated and secured in place before said device is applied.

5. The method of claim 4 wherein said edges are secured by suturing.

6. The method of claim 4 wherein said edges are secured by applying surgical tape.

7. The method of claim 1 wherein an antibiotic ointment is applied to said would through said inner core.

* * * * *